(12) United States Patent
Walter et al.

(10) Patent No.: US 6,599,859 B1
(45) Date of Patent: Jul. 29, 2003

(54) MULCH/HERBICIDE COMPOSITION

(75) Inventors: James Frederic Walter, West Chester, PA (US); Sanford Rush Simon, Sylacauga, AL (US)

(73) Assignees: Dow AgroSciences LLC, Indianapolis, IN (US); U.S. Fertilizer Corporation, Birmingham, AL (US)

( * ) Notice: Subject to any disclaimer, the term of this patent is extended or adjusted under 35 U.S.C. 154(b) by 0 days.

(21) Appl. No.: 10/028,460

(22) Filed: Dec. 20, 2001

(51) Int. Cl.⁷ ................................................ A01N 43/40
(52) U.S. Cl. ............................................ 504/244; 47/9
(58) Field of Search ................................ 504/244; 47/9

(56) References Cited

U.S. PATENT DOCUMENTS

| | | | | | |
|---|---|---|---|---|---|
| 3,590,528 | A | * | 7/1971 | Shepherd | 47/9 |
| 4,692,184 | A | * | 9/1987 | Lee | 71/94 |
| 5,672,434 | A | * | 9/1997 | Dalebroux et al. | 47/9 |

* cited by examiner

*Primary Examiner*—S. Mark Clardy
(74) *Attorney, Agent, or Firm*—Craig E. Mixan; Thomas D. Rogerson

(57) ABSTRACT

The present invention relates to a composition comprising a mulch and an herbicide (i.e., dithiopyr) useful for weed control.

6 Claims, No Drawings

MULCH/HERBICIDE COMPOSITION

The present invention relates to a composition comprising a mulch and an herbicide useful for weed control.

Mulch is a covering spread over the ground that conserves moisture in soil and suppresses the growth of weeds. Mulches provide many advantages to a grower. They help prevent soil erosion and runoff from heavy rain. Moisture in the soil is conserved because evaporation is reduced. In addition, mulches suppress weed growth by either choking the weeds out or by preventing their seeds from contacting the soil. A layer of mulch over soil also acts as an insulator by keeping the soil cool in the summer and helping to eliminate danger to plants from freeze-thaw cycles in the winter. While doing its task of keeping moisture in the soil and suppressing the growth of weeds, mulch also creates a rich unified background for plants, shrubs, and trees. When organic mulch decomposes it becomes a valuable addition to the soil structure.

Many different materials have been used as mulches including pine nuggets, pine needles, shredded hardwood bark, chipped hard wood, sawdust, ground rubber, and plastic mats. Mulches are commonly used in new and existing ornamental beds to protect and beautify both annual and perennial plantings. They are often used in recreational areas around swing sets and climbing bars. Mulch offers several advantages in these areas. It retains soil moisture, protects young plants, suppresses weeds, prevents mud and erosion, adds nutrients to the soil as it decomposes and may add color and texture to the garden. However, one of the biggest deficiencies of mulch is incomplete weed control. Weeds such as nutsedges and thistles can grow through even thick mulch. If the mulch is disturbed or not evenly applied, large numbers of weeds can grow through the mulch.

Because mulches do not entirely control weeds, additional weed control measures must normally be employed in order to ensure a weed-free area. The standard additional weed control measure is to apply one or more herbicides to the area. These applications may be made before, at the same time, or after the mulch itself is spread. Because an additional application is required, additional costs are encountered by the grower. Therefore, it would result in cost savings and increased efficiency if mulch and herbicide combinations could be used. Such combinations are known. Attempts to add herbicides to mulches, especially mulching films, are well known. Unfortunately, adding herbicides to wood mulches has been problematic due to the nature of both the herbicides and the mulch. Most pre-emergent herbicides come from a group of compounds called dinitroanilines. These compounds (including pendimethalin, Prodiamine and Oryzalin) are yellow in color and when added to the mulch give it an unacceptable yellow color. Furthermore, these materials have a strong affinity for organic mater. As a result, they may bind to the mulch and not release to control the weeds. However, we have discovered a mulch/herbicide combination that provides significantly better weed control than would be expected, based on the weed control obtained using the mulch and the herbicide separately.

U.S. Pat. No. 4,692,184 discloses a class pyridinedicarboxylic acid herbicides which are useful for weed control under a variety of conditions. They are particularly effective for pre-emergence or early post-emergence weed control. We have discovered that incorporating these herbicides into a mulch before spreading the mulch provides unexpectedly high herbicidal activity and is effective in controlling a variety of weeds at lower application rates than those expected from separate use of the mulch and the herbicide. This invention solves the problem of the herbicide binding to the mulch by first incorporating the herbicide onto a carrier and then blending the carrier into the mulch. The herbicides of this invention are a unique choice for this use because, unlike the dinitroanilines they are clear white compounds and do not cause staining. This leaves the mulch it's natural color. By incorporating the herbicide onto a clay carrier, and then blending into the mulch, the small clay particles are then free to filter to the ground where it can release the herbicide at the most effective site of action.

One embodiment of this invention provides a composition comprising:
a) an herbicidally effective amount of a compound of the formula (I)

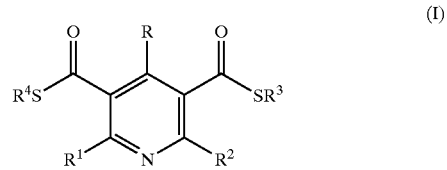

wherein:
R is $(C_1-C_7)$alkyl, $(C_2-C_7)$alkenyl, $(C_2-C_7)$alkynyl, $(C_3-C_7)$cycloalkyl, haloalkyl, or $(C_3-C_6)$cycloalkanylalkyl;

$R^1$ and $R^2$ are independently $(C_1-C_3)$alkyl, fluorinated methyl, or chlorofluorinated methyl, provided that at least one of $R^1$ and $R^2$ is fluorinated methyl or chlorofluorinated methyl; and $R^3$ and $R^4$ are independently $(C_1-C_3)$alkyl; and wherein the herbicide is incorporated onto a carrier; and b) an organic or inorganic mulch.

In a second embodiment of this invention, there is provided a method for controlling weeds comprising applying a composition comprising:
a) an herbicidally effective amount of a compound having the formula (I)

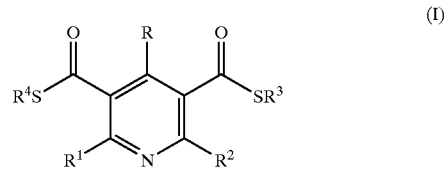

wherein:
R is $(C_1-C_7)$alkyl, $(C_2-C_7)$alkenyl, $(C_2-C_7)$alkynyl, $(C_3-C_7)$cycloalkyl, haloalkyl, or $(C_3-C_6)$cycloalkanylalkyl;

$R^1$ and $R^2$ are independently $(C_1-C_3)$alkyl, fluorinated methyl, or chlorofluorinated methyl, provided that at least one of $R^1$ and $R^2$ is fluorinated methyl or chlorofluorinated methyl; and $R^3$ and $R^4$ are independently $(C_1-C_3)$alkyl; and wherein the herbicide is incorporated onto a carrier, and b) an organic or inorganic mulch; to the locus of the weeds.

The term "alkyl" means a straight or branched alkyl group having one to seven carbon atoms per group such as, for example, methyl, ethyl, n-propyl, isopropyl, n-butyl, isobutyl, sec-butyl and tert-butyl.

The term "alkenyl" means a straight or branched alkenyl group having two to seven carbon atoms per group such as, for example, ethenyl, 2-propenyl, 2-butenyl, 1-methylethenyl, 2-methyl-2-propenyl and the like.

The term "alkynyl" means a straight or branched alkynyl group having from two to six carbons per group such as, for example, ethynyl, 2-propynyl, 2-butynyl and the like.

The term "cycloalkanylalkyl" means an alkyl radical substituted with a $(C_3-C_6)$cycloalkyl radical.

The term "fluorinated methyl" means a methyl group wherein from one to three of the methyl group hydrogens is replaced by a fluorine. The term "chlorofluorinated methyl" means a methyl group wherein at least one hydrogen is replaced by a fluorine and at least one hydrogen is replaced by a chlorine.

"Halo" means chloro, fluoro, bromo and iodo.

The term "locus" means any area where weeds grow or are likely to grow and where the use of mulch is desired.

Preferably R is $(C_1-C_7)$alkyl. More preferably, R is 2-methylpropyl. Preferably, $R^1$ and $R^2$ are independently methyl, fluorinated methyl, or chlorofluorinated methyl. More preferably, $R^1$ and $R^2$ are independently fluorinated methyl or chlorofluorinated methyl. Most preferably, one of $R^1$ and $R^2$ is difluoromethyl and the other of $R^1$ and $R^2$ is trifluoromethyl Preferably, $R^3$ and $R^4$ are independently $(C_1-C_3)$alkyl. Most preferably, $R^3$ and $R^4$ are both methyl.

Most preferably, the herbicide is 2-difluoromethyl-4-(2-methylpropyl)-6-trifluoromethyl-3,5-pyridinedicarbothioic acid, S,S-dimethyl ester, a material commonly referred to as dithiopyr.

The term "mulch" in its broadest sense means any material spread over the ground that conserves moisture in soil and suppresses the growth of weeds. Mulches include organic materials such as, for example, pine straw, shredded pine, shredded hard wood, shredded licorice root, shredded wood waste, shredded cedar, cedar chips, pine bark, pine nuggets, pine needles, shredded wood and bark, chipped wood and bark, sawdust, ground rubber, grass clippings, leaves, straw, hay, compost, newspaper, ground plastic, plastic sheeting, and landscape fabric, as well as inorganic materials such as, for example, stones and marble chips, or combinations thereof.

As used herein, all percentages are percent by weight, unless otherwise specified and are inclusive and combinable. All ratios are by weight and all ratio ranges are inclusive and combinable. All molar ranges are inclusive and combinable.

The method of the present invention may optionally further comprise application of other compounds having biological activity, for example, additional herbicidally active compounds or compounds having fungicidal activity or insecticidal activity, to the locus of the weeds.

The method of the present invention is useful for the control of weeds in many loci, including, for example, agricultural crops, horticultural crops, ornamental crops, flower beds, and in areas surrounding structures, walkways, and driveways.

The herbicide of this invention is incorporated onto a carrier using any common method which will result in distribution of the herbicide onto the surface, the interior, or both, of a solid carrier. Such incorporation can be accomplished in a variety of ways including; a) dissolving the herbicide in a solvent, blending the dissolved herbicide with the carrier, and removing the solvent; b) melting the herbicide, blending the melted herbicide with the carrier, and cooling the blend; c) physically blending solid herbicide with the carrier; and d) similar methods known to those skilled in the formulation arts.

The term "carrier" means one or more solid diluents which can be used to dissolve, disperse or diffuse the herbicide in a composition without impairing the herbicide's effectiveness and which by itself has no significant detrimental effect on the soil, equipment, desirable plants, or agronomic environment. Carriers include, for example, ground natural minerals such as kaolins, clays, talc, chalk, quartz, attapulgite, montmorillonite, calcite, marble, pumice, sepiolite, dolomite, and diatomaceous earth; ground synthetic minerals, such as highly dispersed silicic acid, alumina, and silicates; synthetic granules of inorganic and organic meals; granules of organic material such as sawdust, coconut shells, corn cobs, and tobacco stalks; and synthetic polymeric materials. Preferably, the carrier is a clay.

The composition of this invention may, in addition to the herbicide and the carrier, also contain inert ingredients. Such ingredients include surfactants, dispersants, spreaders, stickers, antifoam agents, emulsifiers, and other similar materials such as those described in McCutcheon's Emulsifiers and Detergents, McCutcheon's Emulsifiers and Detergents/Functional Materials, and McCutcheon's Functional Materials, all published annually by McCutcheon Division of MC Publishing Company (New Jersey, USA). Inert ingredients may be added to the composition at the same time or in a separate impregnation step occurring before or after the herbicide is impregnated onto the carrier or in multiple impregnation steps occurring before, at the same time, and/or after the herbicide is impregnated onto the carrier. This invention also contemplates compositions which include one or more additional pesticides and/or one or more fertilizing materials. Fertilizing materials may function as the carrier, may be impregnated onto the carrier, or be separately added to the mulch.

The herbicide can be incorporated onto the carrier at concentrations up to 5 percent, by weight. Preferably, the herbicide is incorporated at concentrations of from 0.001 to 1 percent, by weight; more preferably from 0.001 to 0.01 percent, by weight. The amount of carrier impregnated herbicide which is blended into the mulch will vary depending upon the type of mulch material and the desired depth of the mulch. The mulch may be spread over the area to be treated at any depth which is typically used for standard mulching. This may be up to 15 cm. However, more typically, mulches are spread to a depth of from 5 to 10 cm. Based upon the desired depth of mulch, the amount of carrier-incorporated herbicide should be in the range of from 100 to 1000 grams per hectare; preferably 200 to 600 grams per hectare; most preferably 400 to 500 grams per hectare.

The following examples illustrate a number of embodiments of this invention.

In the following examples, dithiopyr is first dissolved in a warm solvent such as dipropylene glycol at 12–18 percent, by weight. This solution was then sprayed onto a clay carrier. The clay carrier was then blended with mulch so that when applied to the ground the dithiopyr had a application rate of 370 or 560 grams per hectare.

The results provided by the composition of this invention were compared with the results obtained using the herbicide and the mulch individually.

| Treatment | Dithiopyr Application Rate | % Weed Control |
|---|---|---|
| None | — | 0 |
| Dithiopyr[1] | 560 | 30 |
| Pinebark Mulch (5 cm deep) | — | 30 |
| Hardwood bark mulch (5 cm) | — | 30 |
| Pinebark Mulch (5 cm) + dithiopyr | 370 | 75 |
| Hardwood bark mulch (5 cm) + dithiopyr | 370 | 75 |

-continued

| Treatment | Dithiopyr Application Rate | % Weed Control |
|---|---|---|
| Hardwood bark mulch (7.5 cm) | — | 70 |
| Pinebark mulch (7.5 cm) | — | 55 |
| Hardwood bark mulch (7.5 cm) + dithiopyr | 560 | 90 |
| Pinebark mulch (7.5 cm) + dithiopyr | 560 | 90 |

[1]= Dimension ™ Turf and Ornamental Herbicide 12.7 percent by weight dithiopyr

We claim:

1. A composition comprising:
    a) an herbicidally effective amount of the herbicide dithiopyr wherein the herbicide is incorporated onto a solid carrier; and
    b) an organic or inorganic mulch.

2. The composition of claim 1, wherein the carrier is a clay.

3. The composition of claim 1, wherein the mulch is selected from one or more of pine straw, shredded pine, shredded hard wood, shredded licorice root, shredded wood waste, shredded cedar, cedar chips, pine bark, pine nuggets, pine needles, shredded wood and bark, chipped wood or bark, sawdust, ground rubber, grass clippings, leaves, straw, hay, compost, newspaper, ground plastic, plastic sheeting, landscape fabric, stones, and marble chips.

4. A method for controlling weeds comprising applying a composition comprising:
    a) an herbicidally effective amount of the herbicide dithiopyr wherein the herbicide is incorporated onto a solid carrier, and
    b) an organic or inorganic mulch;
to the locus of the weeds.

5. The method of claim 4, wherein the carrier is a clay.

6. The method of claim 4, wherein the mulch is selected from one or more of pine straw, shredded pine, shredded hard wood, shredded licorice root, shredded wood waste, shredded cedar, cedar chips, pine bark, pine nuggets, pine needles, shredded wood and bark, chipped wood or bark, sawdust, ground rubber, grass clippings, leaves, straw, hay, compost, newspaper, ground plastic, plastic sheeting, landscape fabric, stones, and marble chips.

* * * * *